United States Patent [19]

Kass

[11] Patent Number: 4,996,040
[45] Date of Patent: Feb. 26, 1991

[54] CELLS STAINED WITH A DIAZO DYE

[75] Inventor: Lawrence Kass, Hinckley, Ohio

[73] Assignee: Cytocolor, Inc., Hinckley, Ohio

[21] Appl. No.: 373,269

[22] Filed: Jun. 29, 1989

Related U.S. Application Data

[63] Continuation-in-part of Ser. No. 148,668, Jan. 26, 1988, Pat. No. 4,853,210, which is a continuation-in-part of Ser. No. 604,741, Apr. 27, 1984, abandoned.

[51] Int. Cl.[5] .............................................. G01N 33/48
[52] U.S. Cl. ......................................... 424/3; 534/761
[58] Field of Search ........................... 424/3; 548/267; 534/761

[56] References Cited

U.S. PATENT DOCUMENTS 3,706,725  12/1972  Ozutsumi et al. .................... 534/761
4,853,210  8/1989   Kass ......................................... 424/3

Primary Examiner—Mukund J. Shah
Assistant Examiner—E. C. Ward
Attorney, Agent, or Firm—Pearne, Gordon, McCoy & Granger

[57] ABSTRACT

This invention relates to the cytology of blood, bone marrow, and lymph node cells, and to the composition and method of differentiating, identifying, and enumerating said cells among a plurality of cells of hematopoietic origin. More specifically, the invention is directed to the use of basis cationic diazo dyes capable of staining a plurality of cells of hematopoietic origin to differentiate and enumerate the abnormal from the normal cells. The stained cells obtained by this invention have individual color characteristics which permit the identification and differentiation by use of various optical instruments, including, for example, an image analyzer, microscope, photomicroscope and the like.

10 Claims, 1 Drawing Sheet

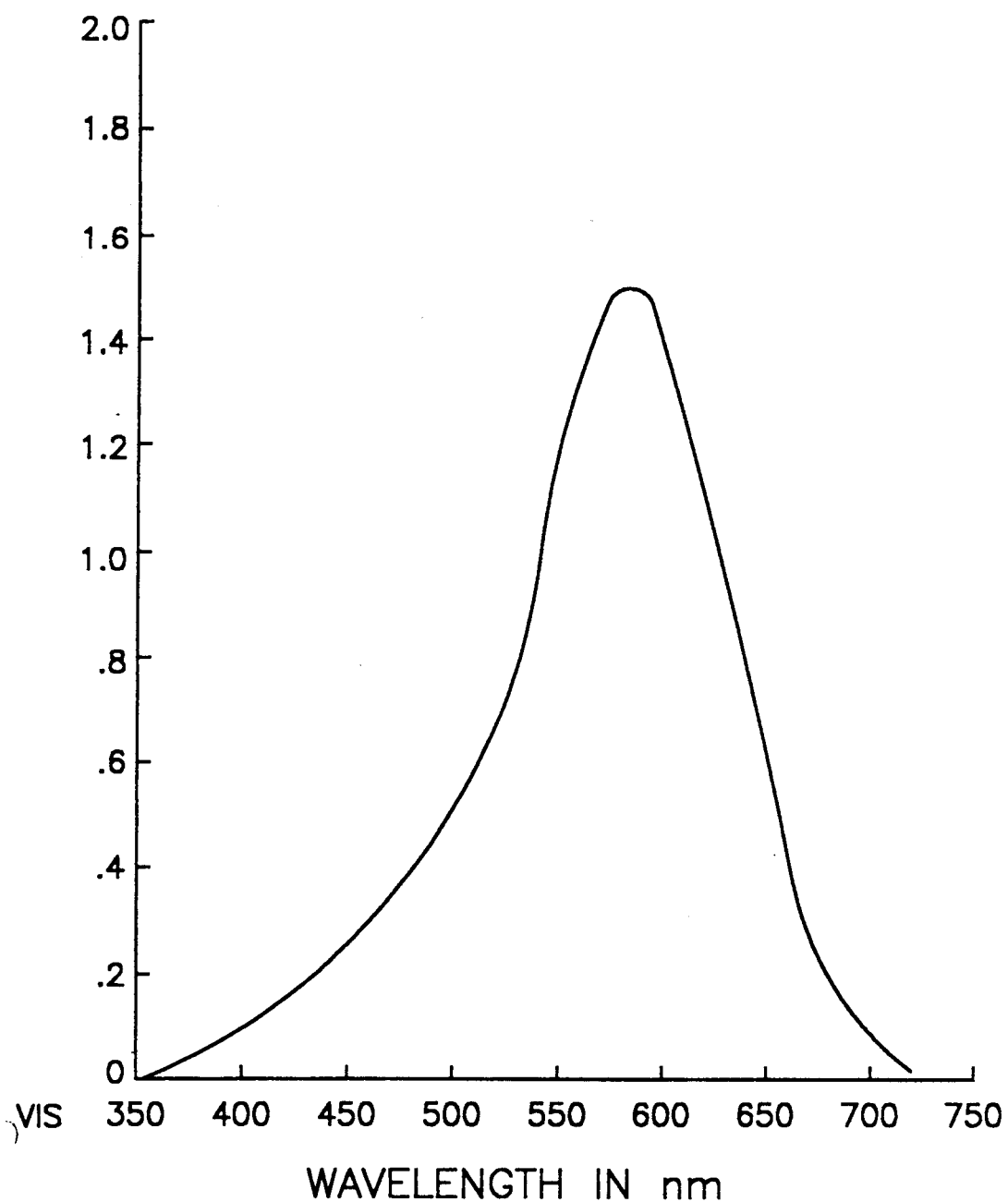

CELLS STAINED WITH A DIAZO DYE

CROSS REFERENCE TO RELATED APPLICATIONS

This application is a continuation-in-part of copending application Ser. No. 07/148,668 filed Jan. 26, 1988 (U.S. Pat. No. 4,853,210), which in turn is a continuation-in-part of copending application Ser. No. 06/604.741, filed Apr. 27, 1984, entitled "Identification of Myeloblast and Other Immature Granulocytic Cells." now abandoned.

BACKGROUND OF THE INVENTION

This invention relates to the use of a heterocyclic diazo dye for the cytological preparation of a biopsy specimen derived from blood, bone marrow, lymph nodes, and other specimens of hematopoietic origin. More specifically, this invention relates to the method of using a basic cationic diazo dye known as "Basic Blue 93" for staining dried or fixed specimens of human blood and bone marrow cells. The diazo dye reacts with the lysosomes (primary granules) in the cells of the neutrophilic granulocytic series providing a composition to identify and differentiate between the myeloblasts and the lymphoblasts prior to treating leukemic patients.

The use of cationic water-soluble heterocyclic diazo dyes of this invention is an advance over the prior art (Romanowsky and Malachowski) where mixtures of dyes were used for staining biopsy specimens. The stained cells of hematopoietic origin obtained in accordance with this invention provide excellent color stability and are exceptionally clear with respect to cellular detail and brilliance of the cell structure.

The diagnosis of hematological disorders has been accomplished, in part, by the enumeration and identification of formed elements of the peripheral blood and bone marrow. The basis of hematological diagnosis has been microscopic examination of a panoptically stained specimen of blood or marrow which provides sufficient information to make a diagnosis. In addition to the developments in panoptic light microscopy, cytochemical stains were developed to identify cell types more precisely than was possible by using panoptic stains. Cytochemistry is biochemistry on a microscopic and submicroscopic level applied to cells and tissues. The cytochemical stains identify enzymes, substrates, and organelles. Cytochemical stains can be selective for one cell type compared to another and, as such, these stains have been used as diagnostic tools, especially in making distinctions between the various cytologic types of acute leukemias and preleukemic disorders.

With the development of new synthetic organic dyestuffs, it was found that, by adding these dyes to freshly obtained specimens of blood, some cells stained with one or more dyes, where others did not. Interest in supravital stains is based on the ability of some of these dyes to stain a reticulated network in young erythrocytes. The demonstration of reticulocytes by the supervital technique is still a standard laboratory test in hematological diagnosis Following the developments in supravital staining of blood, Ehrlich appreciated the need for more stable, competent preparations of blood that could be examined under the microscope. Ehrlich devised stains comprising Orange G, acid fuschin, and methyl green. By using this mixture of dyes. Ehrlich identified and named most of the blood leukocytes based on differential staining as we know them today. With the recognition that some of the available dyes caused differential coloration of blood cells, others modified Ehrlich's stain, including, for example, the Romanowsky method, followed by Wright, Jenner, May, and Grunwald and Giemsa's method. All of these modifications included a mixture comprising several basic cationic dyes.

It was discovered early in the history of morphologic and cytochemical diagnosis of blood disorders that the examination of only panoptically stained specimens of blood or bone marrow was not sufficient to make a diagnosis. By using cytochemical stains, it is possible to identify the presence or absence of substance in one cell type in comparison to another, or the increase or decrease in the quantity of a substance in these cell types. These differences are important diagnostic tools when they reflect differences in one cell type compared to another, and in normal cells compared to pathologic blood cells It is now appreciated that quantitative differences in the intensity of cytochemical stains are important diagnostically. Moreover, the differences in the configuration and spatial distribution of the reaction product can have diagnostic value.

Specific diseases have cytochemical profiles that complement the traditional microscopic examination of panoptically stained preparations. There are a variety of hematologic disorders wherein cytochemical tests have diagnostic value. Complementing the conventional light microscopy of panoptically stained specimens of blood or bone marrow, cytochemical stains have improved the precision of hematological diagnosis with the recognition that these stains can reveal properties that are distinctive for one cell type compared to another. Cytochemical stains have found increased application in the study of blood, lymph node and bone marrow specimens. For the most part, these stains detect increased or decreased amounts of an enzyme or a metabolite that reflect the pathophysiological condition of a disordered cell. While the exact mechanism or chemistry responsible for the production of the cytochemical abnormalities are unknown, many of these abnormalities are sufficiently distinctive to make them useful diagnostically. As a diagnostic tool for cellular hematology, cytochemistry represents a rapid and inexpensive method to distinguish one cell type from another on the basis of characteristic properties, with advances in dye chemistry and the automation of leukocyte counting, one can anticipate further improvements in the cytochemistry of blood cells and the precision of hematological diagnosis in the future. Discussions of cytochemical stains can be found in *New Cytochemical Stains for Blood and Bone Marrow Cells and Cystobiology of Leukemias and Lymphomas*, by L. Kass, M.D., Raven Press New York N.Y., Pages 161–177, 1985, and Lawrence Kass, M.D. *Leukemia Cytology and Cytochemistry*, published by J. B. Lippincott, Philadelphia, 1982.

In erythroblasts, for example, of a patient with erythroleukemia, a PAS (periodic acid-Schiff) stain may reveal large chunklike aggregates of glycogen. In patients with acute lymphoblastic leukemia, the glycogen may appear as smaller punctate aggregates In patients with chronic erythremic myelosis, the pattern of the staining may be diffused and punctate in the same cell, or either diffused or punctate in different cells. The differences in the configuration and spatial distribution of glycogen in different pathologic blood cells may be relevant to the metabolic abnormalities that are unique to each type of cell.

Early in the study of blood cell identification, it became apparent that the differentiation and identification of the early immature or primitive precursor cells in the blood and bone marrow created difficulties when using the Romanowsky type of stains. To circumvent this problem, the cytochemical stains were developed which, when applied to blood and bone marrow cells, identified the mature cells and their primitive or immature precursors on the basis of a characteristic property such as a unique enzyme or cellular metabolic, rather than on the physical features, such as size, shape, and color. The earliest cytochemical stains to be applied to the blood and bone marrow cell for identification were the peroxidase stains. It has become apparent that some cells contain peroxidase activity (granulocytes) while other cells (lymphocytes) do not. Not long afterwards, the peroxidase stain was used in the study of immature or permanent cells in acute leukemia. Thus, for the first time it became possible to distinguish immature or primitive granulocytic cells, i.e., myeloblasts, from immature lymphoid cells or lymphoblasts. This distinction could be achieved on the basis of the detection of myeloperoxidase activity in myeloblasts, but not in lymphoblasts.

It is a practice in cytochemical staining of myeloperoxidase to add a color-forming compound, and exogenous chromogen, such as benzidene or o-tolidine coupled with an oxidizing agent, such as hydrogen peroxide. Benzidene, however, is a carcinogen, and therefore a potential hazard to the user. The reaction product obtained is, unfortunately, unstable, and fades over a period of time. Moreover, some of the leukemic myeloblasts presently being identified as myeloblasts with monoclonal antibodies do not contain a demonstrable peroxidase activity. Over the past several decades, other tests have been devised as alternatives to the myeloperoxidase reaction because of these limitations.

One of the alternative tests was the use of a Sudan Black stain. The Sudan Black stain is known as CI 26150. When applied to fixed preparations of blood and bone marrow cells, Sudan Black B stains lipids in the granules of granulocytic cells at all stages of their development. The stain is weakest when used in conjunction with immature granulocytic cells, like myeloblasts and promyelocytes. It is strongest in mature granulocytic cells, such as neutrophils, eosinophils, and basophils. Although useful in the laboratory for distinctive identification between leukemic myeloblasts and leukemic lymphoblasts, Sudan Black B stains show poor localization in granular structures. Moreover, there is considerable non-specific background precipitation of the dye in many of the contemporary methods where it is used.

Along with the development of Sudan Black B as an alternative to the traditional myeloperoxidase reaction, a specific esterase enzyme was identified as unique to the cells of the granulocytic series. By using naphthol-ASD-chloroacetate as the substrate and a sensitized dye such as Blue BBN as the indicator, the specific esterase stain demonstrates granulocytic properties in immature cells like the myeloblasts in acute myeloblastic leukemias, or in granulocytic sarcoma (chloroma). This stain and methods of using the stain for this purpose have several shortcomings, which include the need for an exogenous substrate, with a sensitized unstable dye coupler, imprecise localization of the reaction product in granules, need for a nuclear counterstain, prolonged incubation period to perform the test, and considerable background precipitation of the coupler, making it difficult to distinguish between artifact and the reaction product.

As a result of these shortcomings of the specific esterase reaction, other stains have been developed as an alternative. Used as a direct stain applied to a fixed preparation of blood and bone marrow cells, these stains were simpler for application than the traditional stains, and have produced comparable results. Complexities associated with the specific esterase reaction tests led to the discovery that chlorozol Black E (direct Black 38, CI 30235) wherein both the primary granules or lysosomes, and secondary granules or specific granules have been distinguished and demonstrated in neutrophilic granulocytic cells on the basis of identifiable differences. Using Saturn Blue, CI 42045, also known as "Acid Blue 1," similar differences in the primary and secondary granules have been noted. In the use of Niagara Sky Blue 6B, CI 24410, known also as "Direct Blue 1," identifiable differential coloration of primary and secondary granules provided an advance in the art. With an acid dye, known as "Sulfonaphthyl Red," an acid dye not identified by the Color Index number, both primary and secondary granules are stained red. As presently known, there is no dyestuff reported which will selectively and preferentially stain only the primary granules or lysosomes in a dried and/or fixed cell of the neutrophilic granulocytic series, including the myeloblast, promyelocytes, myelocytes, bands, and neutrophils. None of the dyes known heretofore have been sufficiently selective, since they stained both the primary and secondary granules, producing in some instances a color difference.

Accordingly, it is an object of this invention to provide a water-soluble cationic diazo dye useful in staining unfixed and/or fixed cells of the neutrophilic granulocytic series.

It is another object of this invention to provide cells of a hematopoietic origin fixed and subsequently stained with a water-soluble cationic diazo dye to obtain stained cells having individual color characteristics which permit the differentiation, identification, and enumeration thereof by use of an optical instrument.

It is still a further object of this invention to provide a plurality of cells of hematopoietic origin stained with effective amounts of water-soluble cationic diazo dyes.

These and other objects of the invention will become apparent from a further and more detailed description of the invention.

SUMMARY OF THE INVENTION

This invention is directed to a combination of a diazo dye and a biopsy specimen and the method of differentiating, identifying, and enumerating normal and abnormal cells among a plurality of cells of hematopoietic origin selected from the group consisting of blood cells, bone marrow cells, and lymph node cells. The method comprises staining a biopsy specimen of said cells with an effective amount of a basic water-soluble cationic heterocyclic diazo dye. Preferably, the staining of the specimen takes place in an aqueous environment, i.e., an aqueous solution of the cationic diazo dye. The cells e.g., human blood cells, may be dried or unfixed or, in the alternative, fixed in an organic fixative such as absolute methyl alcohol or in an aqueous solution of a lower molecular weight alcohol, which may contain up to 10% by weight, and preferably from about 0.05% to 1.0% by weight of the cationic diazo dye of this invention.

The cells derived from a biopsy specimen in accordance with this invention include blood cells, lymph node cells, and bone marrow cells of hematopoietic origin which include both the normal and abnormal cells, i.e., the plurality of cells may include stained cells having individual color characteristics which permit the differentiation, identification, and enumeration of each stained cell. The stained cells may be differentiated by use of various optical instruments, including a microscope, image analyzer, and various other optical diagnostic instruments.

BRIEF DESCRIPTION OF THE DRAWING

The drawing is the absorption spectra of Basic Blue 93.

DETAILED DESCRIPTION OF THE INVENTION

The heterocyclic diazo dyes of this invention are water-soluble basic cationic dyes which preferentially and selectively stain primary granules or lysosomes in cells of the neutrophilic granulocytic series. A specific cationic diazo dye (Basic Blue 93) which is preferred for purposes of this invention is characterized by the formula $C_{24}H_{34}N_9Cl$ and is available under the trademark "AIZEN CATHILON NAVY BLUE RLH." These diazo dyes can be obtained from Hodagaya Chemical Company of Japan. A particular dye, i.e., Basic Blue 93, can be identified by the absorbance spectra as set forth in the drawing.

More specifically, the basic heterocyclic diazo dyes of this invention, including Basic Blue 93, are characterized by formula I or II:

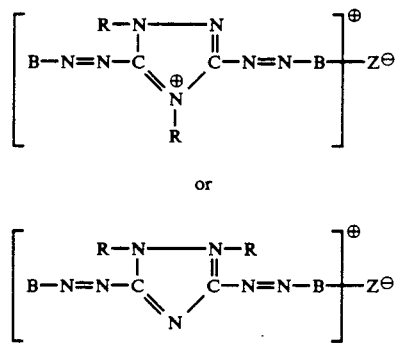

wherein R is a lower alkyl or benzyl radical, $Z^{\ominus}$ is an anion such as chlorine, and B is a radical having the formula:

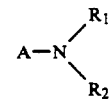

wherein A is a phenylene or naphthylene radical and $R_1$ and $R_2$ are the same or different, and are selected from the group consisting of hydrogen and lower alkyl radicals such as methyl, ethyl, propyl, or butyl groups. Preferably, for purposes of this invention, $R_1$ and $R_2$ are lower alkyl radicals, such as a methyl group, and Z- is an anion, such as chlorine. More specifically, the cationic diazo dyes of this invention have an anion provided by a strong inorganic acid, such as hydrochloric acid. These diazo dyes impart a red-dish-blue or a blue shade to materials such as paper, cotton, and the like. They are water-soluble and are obtained by quaternizing a diazo compound free of the sulfonic or carbonic radicals, and are characterized by the above-identified formulae.

The preferred diazo dye for purpose of this invention is known as Basic Blue 93 available under the name AIZEN CATHILON NAVY BLUE RLH, which has the formula:

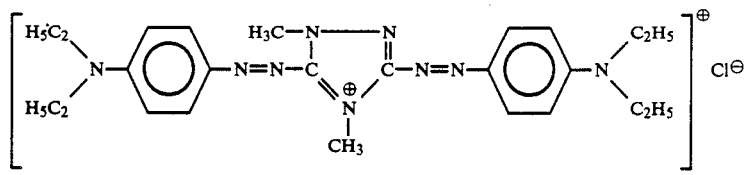

More specifically, the basic cationic diazo dyes of the present invention are disclosed in U.S Pat. No. 3,706,725, which issued on Dec. 19, 1972, to Hodagaya Chemical Co. of Tokyo. Japan, the disclosure of which is hereby incorporated by reference.

As a result of comprehensive testing, it was found that Basic Blue 93, as identified herein, is a dye that preferentially and intensely stains primary granules or lysosomes in cells of the neutrophilic granulocytic series, including the myeloblasts and immature granulocytic cells, and the promyelocytes. For purposes of this invention, the heterocyclic diazo dye is used in concentrations ranging from about 0.05% to 10% by weight, and preferably from about 0.1% to 1.0% by weight in an aqueous solution which may contain a buffering agent. The color of the aqueous solution of the diazo dye may be described as dark purple.

The preferred laboratory procedure comprises preparing a coverslip with a biopsy specimen such as a human biopsy specimen, e.g., blood, bone marrow, or combinations thereof, imprints of bone marrow iopsy core, lymph node imprints or the like, in absolute methanol or an FAA fixative for about two minutes. An FAA fixative comprises about 90 mls of ethyl alcohol, 5 mls of glacial acetic acid, and 5 mls of 37% formaldehyde. The biopsy specimens may be fixed in the solution for periods ranging from about 3 to 10 minutes, e.g., 3 to 5 minutes. It is understood that the diazo stains of this invention are equally operative in aqueous solutions when applied to dried or unfixed cells. However, there is superior and preferred localization of the reaction between the cells and the dye when the stain is applied to fixed cells.

Fixatives are generally classified into two classes based on their ability to coagulate proteins. The coagulant fixatives include, for example, the absolute alcohols such as methanol or ethanol, formaldehyde, trichloroacetic acid, picrics, etc. The ideal fixative should not shrink nor swell the tissue under examination or change the size thereof. However, most fixatives result in some shrinkage or swelling of the tissue. The degree of alteration depends on the nature of the tissue and the fixative employed. In general, anhydrous fixatives such as acetone or absolute alcohols cause shrinkage. A typical example of fixing lymph node tissue is accomplished by using a neutral buffered solution of formalin or absolute alcohols such as methanol. A buffered solution of formalin is an excellent general purpose fixative in that it has the ability to add to the side groups of certain amino acids and thereby denatures the protein and renders it insoluble. Absolute alcohol such as methanol or other anhydrous fixatives are capable of denaturing protein by coagulation and rapid dehydration. Fixatives useful for purposes of this invention, e.g., testing of blood and the like, are well known and may be found in the text incorporated herein by reference, by S. W. Thompson and R. D. Hunt entitled *Selected Histochemical and Histopathological Methods*, published by Charles C Thomas, Springfield, Ill.

The slide preparation containing the fixed specimen was rinsed in distilled water. An aqueous solution of the Basic Blue 93 dye of this invention is applied to the rinsed surface of the specimen and stained for about 5 minutes, washed again with distilled water to remove any excess dye, and mounted with a synthetic resin-based medium such as Permount or its equivalent on a clean glass slide for normal light microscope examination. Upon examination of normal peripheral blood samples, only a few tiny black granules were observed in normal neutrophils and bands. More granules were observed in the field with bands than were apparent with the neutrophils. Black granules of the type found in the neutrophils were not visually apparent among the eosinophils, basophils, lymphocytes, monocytes, erythrocytes, or platelets.

Normal bone marrow aspirates stained with Basic Blue 93 of this invention revealed nuclei of all cells to be stained pale purple, whereas the cytoplasm of the cells were less red, i.e., a pale lavender.

In cells of the neutrophilic granulocytic series, primary granules or lysosomes were stained an intense black. The promyelocytes also exhibited large numbers of granules which were stained black. In studying the myelocytes, a fewer number of the granules were noticed, as compared with the promyelocytes. However, among the metamyelocytes, bands, and the neutrophils, only a few tiny black granules were observed. The granules in the basophils and eosinophils were stained from a pale lavender to a cream color. No black granules were observed. Moreover, no black granules were found among the megakaryocytes, mast cells, plasma cells, erythroblasts, and histiocytes of normal bone marrow aspirates.

An examination of the leukemic lymphoblasts stained with Basic Blue 93 revealed both nuclei and cytoplasm to be stained a pale purple. No black granules were detected Prominent darker purple aggregates of the nuclear chromatin were observed in the nuclei of leukemic lymphoblasts stained with the Basic Blue 93. In leukemic myeloblasts from patients with acute myeloblastic leukemia, black granules were found, their numbers varying in the cytoplasm of many of the leukemic blasts. These observations were confirmed in parallel slides where peroxidase stain and Sudan Black B stains also gave similar positive confirmation. However, in some instances, where the parallel and comparative slides in which Sudan Black B stain and the peroxidase stain were negative in response, the Basic Blue 93 dye staining was positive. The leukemic blasts were confirmed to be myeloblasts when checked through use of a monoclonal antibody.

Leukemic blasts from patients known to suffer acute promyelocytic leukemia, stained with Basic Blue 93 as indicated above, revealed a large number of black-stained granules. Auer rods, a marker for leukemic blasts of granulocytic origin, also stained black.

Biopsy specimens from patients with acute myelomonocytic leukemia, similarly stained, showed leukemic monocytes having a few black granules in the cytoplasm, which confirms the granulocytic origin of the cells Leukemic monocytes from a patient known to suffer from acute histiomonocytic leukemia, comparatively examined, did not reveal the presence of black-stained granules.

Prior art stains presently known and used to identify cells of the neutrophilic granulocytic series, including as an illustration the myeloperoxidase, Sudan Black B specific esterase, and the new stains among which are direct black 38 and acid blue 1, lack the following important advantages when compared to the Basic Blue 93 of this invention.

In comparison, by using a cationic Basic Blue 93 dye of this invention, it was found that the identification of both the myeloblasts and promyelocytes was more acute than heretofore, due to the unusual precise localization of the dye-cell reaction product in the lysosomes of immature granulocytic cells. The dye-cell reaction product is black. It is easily visible in contrast to the pale lavender color of the nucleus. The Basic Blue 93 dye differentially stains both nucleus and granules, and thus a separate counterstain for the nucleus is unnecessary. The Basic Blue 93 dye is both selective and specific for primary granules (lysosomes). Cells, including the myeloblasts, promyelocytes, and myelocytes containing a predominance of these granules, are more accurately differentiated and identified than heretofore.

Virtually no confusing background precipitates occur. The problem of delineation between reaction products and non-specific precipitation was minimal. The addition of an exogenous substrate, as in the specific esterase reaction for example, or the addition of oxidizing agents such as hydrogen peroxidase, as in the myeloperoxidase reaction, is no longer required.

Dye couplers, which require pre-sensitization before being used, such as hexazotization of a coupler in the specific esterase reaction, are also no longer required. The dye specimen reaction product shows no detectable fading with time (tests over a year). The dye is applicable to the immediate and rapid diagnosis of acute leukemia, where delay in institution of treatment may be detrimental. This contrasts with the use of the prior art specific esterase reaction where incubation may require as long as 30 minutes. Delineation of the nuclear chromatin in the identification of leukemic lymphoblasts is made more specific and definite.

The following are illustrations of comparing diagnostic studies of patients using a diazo dye. i.e. Basic Blue 93 dye of this invention. In all examples fixed biopsy specimens were compared.

EXAMPLE 1

A 40-year old white male was admitted to the hospital with fever and chills. On physical examination, he had normal vital signs. The liver and spleen were enlarged Laboratory values included hemoglobin 8.2 gm%, white blood cell count 135,000/mm$^3$, and platelet count 32,000/mm$^3$.

On Wright's stain of the peripheral blood and bone marrow, many of the cells were leukemic blasts with delicate nuclear chromatin pattern and basophilic cytoplasm devoid of granularity.

Using Sudan Black B and myeloperoxidase staining, a few of the leukemic blasts showed activity of peroxidase and faint staining with Sudan Black B.

Using Basic Blue 93, many of the leukemic blasts contained black punctate granules in the cytoplasm, indicating more clearly their granulocytic origin than was manifest in the use of Wright's stain and Sudan Black B.

Diagnosis made: Acute myeloblastic leukemia.

EXAMPLE 2

A 38-year old black female was admitted to the hospital because of nosebleeds On physical examination, her vital signs were normal The patient had slightly enlarged lymph nodes in the neck and groin Laboratory data included hemoglobin 7.1gm%, white blood cell count 83,000/mm$^3$, and platelet count 22,000/mm$^3$. Evidences of disseminated intravascular coagulation, with low level of fibrinogen, and increased levels of fibrin split products were observed.

On Wright's stain of peripheral blood and bone marrow, many leukemic blasts were seen. Some blasts contained multiple Auer rods and many granules.

Using Sudan Black B and myeloperoxidase stains, a few granules and Auer rods could be recognized in the leukemic blasts.

Using Basic Blue 93, many granules were seen in the leukemic blasts Granules stained an intense black. Multiple Auer rods were easily isolated and identified by characteristic shape and intense black color. More Auer rods and more granules were enumerated than with comparative use of the prior art dyestuffs above.

Diagnosis made: Acute promyelocytic leukemia.

EXAMPLE 3

A 22-year old white male was admitted to the hospital complaining of weakness and fatigue. Physical examination showed patient with normal vital signs. Enlarged lymph nodes and enlarged liver and spleen were detected Laboratory values included hemoglobin 6.3 grams%, white blood cell count 5,600/mm$^3$, and platelet count 12,000/mm$^3$.

Wright's stain of his peripheral blood and bone marrow showed large numbers of leukemic blasts with coarse appearing nuclear chromatin and basophilic cytoplasm devoid of granularity.

Using Sudan Black B and myeloperoxidase stains, no granules were found to be identified in the cytoplasm of the leukemic blasts and the distinctive features of nuclear chromatin could not be identified.

Using Basic Blue 93, no granules were seen in the leukemic blasts. Nuclear chromatin displayed a distinctive pattern of prominent lavender/purple colored aggregates. None of the above stains developed a similar visible pattern of nuclear aggregates in the leukemic blasts.

Using specific monoclonal antibodies, the diagnosis of acute lymphoblastic leukemia was confirmed.

EXAMPLE 4

Upon hospital admittance of a black female, aged 34, experiencing fever and pain in the right upper quadrant, physical examination reported a temperature of 101° and tenderness to palpitation in the pain area. Laboratory reports detailed hemoglobin 13 gram%, white blood count 22,000/mm$^3$, and platelets 300,000/mm$^3$ Ultrasound gall bladder examination showed multiple stones present.

Wright's stain of peripheral blood reported larger numbers of neutrophils, bands, and a few metamyelocytes were reported.

On staining with myeloperoxidase, activity of the enzyme was found in all granulocytic cells, particularly promyelocytes and myelocytes.

Sudan Black B confirmed staining of neutrophils

Using Basic Blue 93, intense black granules were found in more numerous frequency in the promyelocytes and myelocytes. Relatively few granules were observed in granulocytic bands and neutrophils The granules were, when present, more numerous and more intensely stained than with the prior art stains above. Identification of immature leukocytes was more certain with the Basic Blue 93 dye stain. Bone marrow examination showed no evidence for leukemia.

The diagnosis of neutrophilic leukocytosis with "shift to the left" resulted. After cholecystectomy, the patient's blood counts returned to normal.

EXAMPLE 5

An oriental female, aged 38 years, was admitted to the hospital with a rapidly enlarging mass in the left cervical area. Physical examination established presence of 3×4 cm mass and normal vital signs Laboratory analysis included hemoglobin 14 grams%, white blood cell count 8,500/mm$^3$ with normal differential and platelet count 205,000/mm$^3$. The biopsied mass proved to be an abnormal lymph node. A plurality of lymph node imprints were made.

Wright's stain indicated the presence of a large number of primitive appearing cells.

Tests with stains for myeloperoxidase, specific esterase and Sudan Black B established a few of the cells to contain a black reaction product, suggesting their granulocytic origin.

Further checking with Basic Blue 93 established many of the primitive cells contained numerous black, granular reaction products more prominent than observed in the prior tests above. Identification of immature leukocytes was more precise.

Granulocytic sarcoma (chloroma) was diagnosed Within 4 months, the patient expired with acute myeloblastic leukemia.

In the above examples, the human biopsy specimens were fixed, e.g., in an alcohol such as absolute methyl alcohol or formaldehyde solutions, before staining with the cationic Basic Blue 93 dye. However, it has been determined that the Basic Blue 93 dye is completely operative when applied on or to a dried or unfixed cell in an aqueous environment, i.e.. water solution. Moreover, the use of a fixed cell provides a more rapid, sharply localized reaction product, and the nuclear detail is improved. Oddly, the dye appears to act both as a fixative and as a stain. However, it should be noted that the Basic Blue 93 dye is not operative as a supervital stain for lysosomes.

More specifically, in accordance with this invention, cells of hematopoietic origin can be initially exposed or treated with a fixative, e.g., an alcohol such as methanol, at ambient temperatures. After washing off the fixative with water and/or alcohol, etc., the fixed cells are subsequently stained with staining amounts of an aqueous solution comprising from about 0.05% to 10% by weight of a cationic diazo dye.

For purposes of this invention, the term "effective amount" means as little as about 0.05% up to about 10% by weight of the diazo cationic dye. e.g., Basic Blue 93 dye in an aqueous solution. Preferably, the fixed or unfixed cells derived from a human biopsy specimen are stained with the Basic Blue 93 dye in an amount of at least 0.1 part by weight of the dye in an aqueous and/or an alcohol solution. Preferably, the aqueous solutions are buffered with an alkaline buffering agent. As indicated herein, it is common practice to add buffering agents to correct the hydrogen and hydroxyl ion concentration of the aqueous system. Buffering agents should be used in the lowest possible concentration to adjust the ion concentration of the particular medium. The buffering capacity of a buffering system is referred to as its "beta" value, and is defined as the amount of acid or alkaline needed to change the pH by 0.1 unit. Buffering agents are recognized as belonging to several categories including a wide variety of acids, bases, and salts, including acetic acid, ammonium chloride, ammonium hydroxide, the alkali metal salts such as lithium hydroxide, lithium chloride, sodium hydroxide, potassium hydroxide, the alkali metal phosphates, the alkali metal acetates, metal carbonates, bicarbonates, borates, and the like. Buffering systems can be prepared from any of these acids, bases, or salts. Buffering agents useful for purposes of this invention can be found in the text, incorporated herein by reference, by Williams and Chase, entitled *Methods in Immunology and Immochemistry*, Vol. II, Academic Press, N.Y. (1968).

In comparison to the conventional Romanowsky stains, the Basic Blue 93 dye of this invention provides a clearer detail of nuclear chromatin and more a brilliant coloration of the granules For example, the identification of established populations of leukocytes including the T-cells, B-cells and related sub-populations of lymphocytes, i.e., the T-suppressor cells, T-helper cells, and natural killer cells which are known to be important modulators or modifiers of the immune response in normal individuals can now be identified without delay. The identification, differentiation and enumeration of the populations and subpopulations of lymphocytes including the T-cells and B-cells, which are the major lymphocyte population in man, are basic to the understanding of the immune system and the various diseases such as lymphomas, leukemia, and immunodeficiency problems.

B-cells represent about 10 to 20% of the peripheral blood lymphocytes. T-cells which are indicators of the cellular immune responses, i.e., delayed hypersensitivity and graft and an organ transplant rejection, constitute about 70 to 80% of the total. Sub-populations of the lymphocytes known as T-helper cells, and T-suppressor cells, serve to regulate antibody production and are effectors of T-cell function. Enumeration of T-lymphocytes has diagnostic significance in certain chronic disorders where reduced numbers are found. Monitoring the number of T-suppressor and T-helper cells has advanced the understanding the treatment of diseases affecting the immune system. Changes in the ratios of T-helper or T-suppressor cells has been noted as being important in allergy characterization. Monitoring relative changes in these numbers is an indication of a possible rejection in organ surgery transplant.

Chemotherapy patients have been monitored to maintain an immuno-competent state in guiding improvements in the prognosis of cancer patients. Chronic lymphocytic leukemia was often characterized by a monoclonal proliferation of B-cells. More recently, T-helper variant, T-suppressor variant and natural killer cell variant have been observed wherein leukemic lymphocytes share surface antigenic properties found in the corresponding normal lymphocyte subtype. Changes in the ratio of T-helper cells to T-suppressor cells have been frequently found in AIDS (Acquired Immune Deficiency Syndrome). Natural killer cells are postulated to constitute the body's first line of defense against carcinogenic influences. To date, there is no established, reproducible method for identifying the differences between B-cells, T-suppressor cells, T-helper cells and Natural Killer or NK cells with any known panoptic stain. There is no method available for using a single stain of megakaryocytes to identify, distinguish or enumerate these cells from among all other cells in a formalin-fixed biopsy section. Staining of parasitic cells, i.e., cells which contain and/or are surrounded by parasites, in the blood are also accurately delineated. Parasites from individuals known to be victims of parasitic attack such as in tropical fevers, i.e., malaria, due to Plasmodium Falciparum and Trypanosomiasis can be identified by their specific color and patterns.

In addition to the microscopy of panoptically stained specimens of blood or bone marrow, cytochemical stains, such as Basic Blue 93, have improved the precision of hematological diagnosis. It is recognized that Basic Blue 93 can reveal properties that are distinctive for one cell type compared to another, and therefore this stain has found increasing use in the study of blood and bone marrow specimens. For the most part, Basic Blue 93 detects increased or decreased amounts of an enzyme or metabolite that reflects the pathophysiology of a disordered or abnormal cell. Although the exact mechanism responsible for the production of the cytochemical abnormalities is substantially unknown, many of these abnormalities are sufficiently distinctive to make them useful diagnostically. Where it was originally considered a complement to panoptic staining, cytochemistry has now found increasing application as a cellular probe. Moreover, as a diagnostic tool for cellular hematology, cytochemistry represents a valuable and inexpensive method to distinguish one cell type from another on the basis of color characteristics. By utilizing dye chemistry, we can anticipate further improvements in the cytochemistry of blood cells.

While this invention was conceived through optical microscope study and through individual laboratory research, it is well-known to the medical diagnostics arts that optical microscopes have been and are supplanted by many technical advances wherein laser techniques and computer-type instrumentation, for example, have been used to supersede and advance identification, differentiation and enumeration of the normally invisible by improved instrumentation. Thus, the term "microscopic" as used herein is generic to the universe of the infinitely small.

While this invention has been described by a specific number of examples, it is obvious that there are a number of variations and modifications which can be made without departing from the scope of the invention as particularly set forth in the appended claims.

The invention claimed is:

1. A plurality of cells of hematopoietic origin stained with an effective amount of a water-soluble cationic heterocyclic diazo dye; said stained cells having color characteristics permitting the differentiation, identification, and enumeration of the stained cells among a plurality of cells; said cationic heterocyclic diazo dye having the formula I or II:

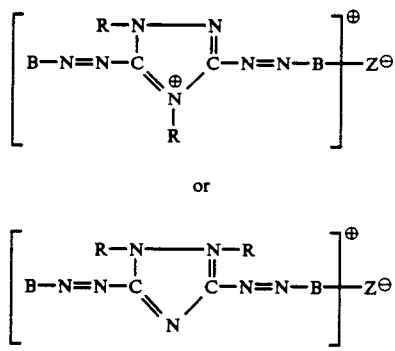

wherein R is a lower alkyl or benzyl radical, $Z^{\ominus}$ is an anion, and B is a radical having the formula:

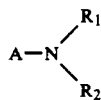

wherein A is a phenylene radical and $R_1$ and $R_2$ are selected from the group consisting of hydrogen and lower alkyl radicals.

2. The plurality of cells of hematopoietic origin of claim 1, further characterized as being selected from the group consisting of blood cells, bone marrow cells, and lymph node cells; wherein the diazo dye is Basic Blue 93 having the formula:

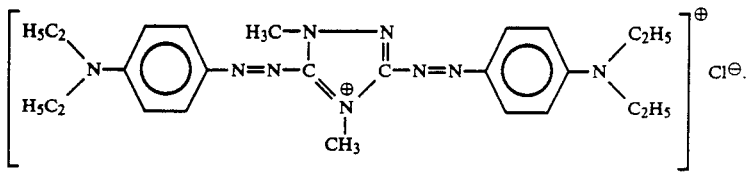

3. The plurality of stained cells of claim 2, further characterized in that the abnormal cells are derived from a human biopsy specimen comprising leukemic cells of granulocytic origin including leukemic myeloblasts and promyelocytes.

4. The plurality of cells of hematopoietic origin of claim 2, further characterized as comprising blood cells, bone marrow cells, and lymph node cells derived from a human specimen.

5. The plurality of cells of claim 4, wherein the human specimen comprises normal and abnormal cells characterized as neutrophilic granulocytic cells.

6. The plurality of cells of claim 5 further characterized in that the neutrophilic granulocytic cells comprise myeloblast, myelocytes, promyelocytes, metamyelocytes, bands and neutrophils.

7. The plurality of cells of claim 5 further characterized in that abnormal cells are derived from a human specimen comprising leukemic cells of granulocytic origin containing leukemic myeloblasts and promyelocytes.

8. The plurality of cells of claim 1 further characterized in that the cells are fixed in an organic fixative and subsequently stained with an aqueous solution containing from about 0.05% to about 10% by weight of the water soluble basic cationic diazo dye.

9. The plurality of cells of claim 8 further characterized in that the cells are fixed in an organic fixative selected from the group consisting of lower molecular weight aliphatic alcohols and aldehydes.

10. The plurality of cells of claim 1 further characterized in that the cells of hematopoietic origin are derived from the human biopsy specimen and stained with an aqueous solution comprising from about 0.1 to 1.0% by weight of the basic cationic diazo dye.

* * * * *